(12) United States Patent
Aspnes et al.

(10) Patent No.: US 6,181,421 B1
(45) Date of Patent: Jan. 30, 2001

(54) ELLIPSOMETER AND POLARIMETER WITH ZERO-ORDER PLATE COMPENSATOR

(75) Inventors: David E. Aspnes, Apex, NC (US); Joanne Yu Man Law, Fremont, CA (US)

(73) Assignee: Therma-Wave, Inc., Fremont, CA (US)

( * ) Notice: Under 35 U.S.C. 154(b), the term of this patent shall be extended for 0 days.

(21) Appl. No.: 09/434,678

(22) Filed: Nov. 5, 1999

(51) Int. Cl.[7] .................................................. G01J 4/00
(52) U.S. Cl. .......................... 356/369; 356/366; 356/367
(58) Field of Search .................................. 356/364, 365, 356/366, 367, 368, 369; 250/225

(56) References Cited

U.S. PATENT DOCUMENTS

| | | | |
|---|---|---|---|
| 3,880,524 | 4/1975 | Dill et al. | 356/118 |
| 3,985,447 | 10/1976 | Aspnes | 356/118 |
| 4,053,232 | 10/1977 | Dill et al. | 356/118 |
| 5,136,597 | 8/1992 | Nightingale | 372/21 |
| 5,245,478 | 9/1993 | Luecke | 359/822 |
| 5,608,526 | 3/1997 | Piwonka-Corle et al. | 356/369 |
| 5,640,412 | 6/1997 | Reed | 372/100 |
| 5,757,494 | 5/1998 | Green et al. | 356/369 |
| 5,798,837 | 8/1998 | Aspnes et al. | 356/369 |
| 5,835,222 | 11/1998 | Herzinger | 356/369 |
| 5,872,630 | 2/1999 | Johs et al. | 356/369 |
| 5,877,859 | 3/1999 | Aspnes et al. | 356/364 |
| 5,946,098 | * 8/1999 | Johs et al. | 356/364 |

OTHER PUBLICATIONS

"Variable Wave Plate" Printed from "http://www.newfocus.com/waveplate.html" on May 12, 1999, 3 pages.
"Refraction of Light, Part II" Printed from "http://acept.la.asu.edu/PiN/rdg/refraction/refraction2.shtml" on Jun. 4, 1999, 4 pages.
"Minimizing Errors in Linear Retarders" Printed from "http://www.meadowlark.com/AppNotes/appnote2.htm", 7 pages.
"Measurement Techniques" Printed from "http://www.sopra-sa.com/mestech.htm" on Jul. 6, 1999, 4 pages.
"Polarization and Polarization Control", New Focus Inc., Santa Clara CA, 8 pages, 1993.
H.G. Jerrard, "Optical Compensators for Measurement of Elliptical Polarization," *Journal of the Optical Society of America*, vol. 38, Nos. 1–12, 1948, pp. cover page, 35–59.

* cited by examiner

*Primary Examiner*—Frank G. Font
*Assistant Examiner*—Sang H. Nguyen
(74) *Attorney, Agent, or Firm*—Limbach & Limbach L.L.P.

(57) ABSTRACT

An ellipsometer for evaluating a sample includes a light generator that generates a beam of light having a known polarization for interacting with the sample. A polarimeter of the ellipsometer includes a compensator, an analyzer and a detector. The compensator is formed of an optically uniaxial material. The compensator has a planar front face, and a planar rear face that is substantially parallel to the front face. The compensator is configured such that one ordinary axis of the crystal, but not the second ordinary axis of the crystal, lies in the plane of the front face. The compensator is positioned in the path of the light beam such that the light beam is normally incident to the front face of the compensator. As such, the ordinary ray is not displaced as it passes through the compensator. The ellipsometer further includes means for rotating the compensator about an axis that is perpendicular to both the front face and to the rear face. The analyzer interacts with the light beam after the light beam interacts with the sample and with the compensator. The detector measures the intensity of the light after the interaction with the analyzer as a function of an angle of the rotation of the compensator about the axis. The measurements can be used to determine the change in polarization state that occurs as light is reflected from the sample.

34 Claims, 3 Drawing Sheets

ELLIPSOMETER AND POLARIMETER WITH ZERO-ORDER PLATE COMPENSATOR

TECHNICAL FIELD

The present invention relates to polarimeters and ellipsometers and, in particular, to a polarimeter or ellipsometer that employs a zero-order plate compensator that is easily calibrated and that exhibits minimal beam displacement.

BACKGROUND

Optically uniaxial materials are commonly used to change the polarization of light. It is well known that optically uniaxial materials operate according to the principle of optical asymmetry—meaning that an electric field oriented along one axis of an optically uniaxial material experiences a dielectric response or refraction index that is different from that of a field oriented along one or both of the other two. The unique axis is known as the extraordinary axis, or optical axis. The other two axes are known as the ordinary axes.

If a light wave incident on optically uniaxial material has electric field components both parallel and perpendicular to the optical axis, the uniaxial material has the effect of changing the relative phase of the components. This slowing of one polarization component relative to the other polarization component is known as "retardation".

A wave plate is a cut slice of optically uniaxial material, usually an optically uniaxial crystal. As is discussed in greater detail below, ideally one would prefer a wave plate where the retardation is less than one wavelength. Such a wave plate is known as a "zero-order" wave plate. Unfortunately, for ultraviolet applications, a zero-order plate made of suitable material would be so thin that it would be virtually impossible, if not impossible, to fabricate.

In some applications, therefore, a multiple-order wave plate is used as a substitute. A multiple-order wave plate operates on the principle that waves repeat themselves every 360 degrees. Therefore, a phase retardation of x+n*360 degrees (where "n" is an integer) is theoretically the same as a phase retardation of x degrees. Unfortunately, multiple-order wave plates have practical disadvantages when compared to zero-order wave plates. One disadvantage is that multiple-order wave plates are much more sensitive to wavelength than zero-order wave plates. Another disadvantage is that the retardation of a multiple-order wave plate is also more sensitive to changes in the angle of incidence of the incident light wave.

It is known that a zero-order wave plate can be constructed from two multiple-order plates of slightly different thicknesses if the extraordinary axis of one is oriented parallel to the ordinary axis of the other. In some configurations, e.g. the Babinet-Soleil compensator, one of the two plates is actually two wedge-shaped pieces such that the effective thickness can be changed by changing their overlap. Thus, some or all of the phase difference caused by the light travelling through the first plate can be cancelled out as the light travels through the second plate. A disadvantage of such "biplate" retarders is that not only do they require two or more elements, but also that the two elements must be aligned very carefully.

It is also known that a compensator can be constructed from a single plate of uniaxial material. (The term "compensator" is used in the art to refer to a retarder whose retardation is adjustable, usually continuously adjustable.) This plate, a Berek's compensator, is a single planar plate of a uniaxial crystal cut such that the extraordinary axis is perpendicular to the plane of the plate. As shown in FIG. 1A, a light beam 102 incident to the plate 104 at normal (90°) incidence travels along the extraordinary axis and therefore for any polarization the electric field experiences the ordinary refractive index, hence no component is phase retarded relative to any other component. Put another way, the velocity of the normally incident light beam 102 through the Berek's compensator 104 is independent of polarization. As shown in FIG. 1B, in operation, to introduce a relative retardation in one of the components, the plate 104 is tilted (for example, by the angle $\Theta_T$) so that one of the field components (denoted in FIG. 1B as $n_c'$) becomes slightly extraordinary. The amount of phase retardation of the output beam 156 relative to the input beam 152 is a function of the angle $\Theta_T$ of tilt.

While Berek's compensators eliminate many of the disadvantages of biplate retarders, they do however have their own disadvantages. One disadvantage is that the crystal must be mechanically tilted to achieve the desired retardation, which requires precision mechanical control. Tilting is particularly difficult when it is also required that the tilted compensator be rotated, such as in an ellipsometer where the compensator is rotated (see below). For example, in such an ellipsometer, the compensator of FIG. 1B may be rotated as denoted by the arrow 158 about the axis defined by the direction of the incident light beam. A further disadvantage of the conventional Berek's compensator is that, in use, the incident light beam is not normally incident (i.e. 90 degrees) to the plate (such as light beam 102 shown in FIG. 1A), so the light beam changes direction at the input air/plate interface (as indicated by beam 155 in FIG. 1B) and at the output plate/air interface due to the difference in refractive index between the air and the plate. This direction change is governed by the well-known Snell's law. So long as the input face of the Berek's compensator is parallel to the output face of the Berek's compensator (for example, as are the faces of the plate 104 shown in FIGS. 1A and 1B), then the direction of the output beam (denoted by reference numeral 106 in FIG. 1A, and by reference numeral 156 in FIG. 1B) is the same as that of the input beam (102 and 152, respectively). This is because, in accordance with Snell's law, whatever angle of direction change occurs at the input face (the light beam within the compensator 104 is denoted in FIG. 1B by reference numeral 155) is reversed at the parallel output face. However, even though there is no difference in direction between the output beam 156 and the input beam 152, the difference in the index of refraction between the Berek's compensator 104 and the air causes the output beam 156 to be displaced laterally from-the input beam 152.

One application in which compensator operation is important is optical ellipsometry. Optical ellipsometry has long been recognized as being a non-destructive technique to provide accurate characterizations of semiconductors and other materials, their surface conditions, layer compositions and thicknesses, and for characterizing overlying oxide layers. This technique is particularly useful to evaluate thickness, crystallinity, composition and index of refraction characteristics of thin films deposited on semiconductor or metal substrates to ensure high yields during fabrication.

By way of background, an ellipsometer probes a sample with a light beam having a known polarization state. The light beam is reflected at non-normal incidence from the surface of the sample. The polarization state of the beam is modified upon reflection in a way that depends upon the properties of the sample. By accurately measuring the polarization state of the reflected beam and comparing it to the original polarization state, various properties of the sample can be ascertained.

In spectroscopic ellipsometry, the probing wavelength is changed and the ellipsometric measurement is repeated at each new wavelength. Spectroscopic ellipsometry is ideal for multi-material samples formed in stacked layers. The different depth penetrations and spectral responses that depend on the material and wavelength of light provide additional information about a sample that is not available from single wavelength ellipsometers.

Many configurations have been proposed to measure the change in polarization state that occurs upon reflection. In one type of ellipsometer only two optical elements are used, a polarizer and an analyzer, one of which is held fixed and the other rotated. Such an ellipsometer, commonly called a rotating-polarizer or rotating-analyzer ellipsometer, is termed "an incomplete" polarimeter, because it is insensitive to the handedness of the circularly polarized component and exhibits poor performance when the light being analyzed is either nearly completely linearly polarized or possesses a depolarized component.

The latter limitations of the rotating-polarizer and rotating-analyzer ellipsometers can be overcome by including a rotatable compensator placed between the polarizer and the analyzer, both of which are now fixed. The compensator can be placed either between the sample and the polarizer, or between the sample and the analyzer. Such a configuration is commonly called a rotatable compensator ellipsometer.

For the purposes of this patent application, a rotatable compensator ellipsometer should be thought of as being generally one at least of two types. With the first type, the compensator is rotated incrementally and stopped at each incremental angle, and data are obtained while the compensator is stationary. With the other type, the compensator is rotated substantially continuously and data are obtained while the compensator is moving. With this latter type of compensator, the obtained data are typically corrected for the averaging that occurs as a result of the compensator moving during a data-acquisition interval.

As discussed above in some detail, the compensator is an optical component that delays the light polarized parallel to its slow axis relative to light polarized parallel to its fast axis by an amount proportional to the refractive index difference along the two directions and the thickness of the plate, and inversely proportional to the wavelength of the light.

Unfortunately, as also discussed above, conventional compensators have characteristics that make them difficult to use, or that make it more difficult to obtain precise results. For example, the displacement phenomena of Berek's compensators causes a light beam passed through the rotatable compensator of an ellipsometer to rotate in a circle along with the compensator. Therefore, what is desired, particularly for use in optical ellipsometry but not necessarily limited to this application, is a compensator that is relatively uncomplicated to operate and does not detract from the accuracy of the ellipsometry results.

SUMMARY

An ellipsometer for evaluating a sample includes a light generator that generates a beam of light having a known polarization for interacting with the sample, A compensator of the ellipsometer is formed of a uniaxial crystal. The compensator is a zero-order compensator having a planar front face, and a planar rear face that is substantially parallel to the front face.

The compensator is configured such that one ordinary axis of the crystals, but not the second ordinary axis of the crystal lies in the plane of the front face. The compensator is positioned in the path of the light beam such that the light beam is normally incident to the front face of the compensator. As such, the direction of the propagation vector is not changed as the light beam enters and exits the compensator.

The ellipsometer further includes means for rotating the compensator about an axis that is perpendicular to both the front face and to the rear face. An analyzer interacts with the light beam after the light beam interacts with the sample and with the compensator. A detector measures the intensity of the light after the interaction with the analyzer as a function of an angle of the rotation of the compensator about the axis. The measurements can be used to determine the change in polarization state of light upon reflection from the sample.

The invention also encompasses a polarimeter alone, such as the polarimeter portion of an ellipsometer. The polarimeter portion of the ellipsometer includes the rotatable zero-order compensator (that has a planar front face, has a planar rear face that is substantially parallel to the front face; and is configured such that one ordinary axis of the crystal, but not the second ordinary axis of the crystal, lies in the plane of the front face). The polarimeter further includes the analyzer and the detector. The polarimeter can be used to analyze the polarization state of any light beam and is not limited to analyzing the polarization state of a light beam reflected off a sample.

BRIEF DESCRIPTION OF FIGURES

FIG. 1A shows the Berek's compensator in an untitled position and FIG. 1B shows the Berek's compensator in a tilted position.

DETAILED DESCRIPTION

Figure 1A:
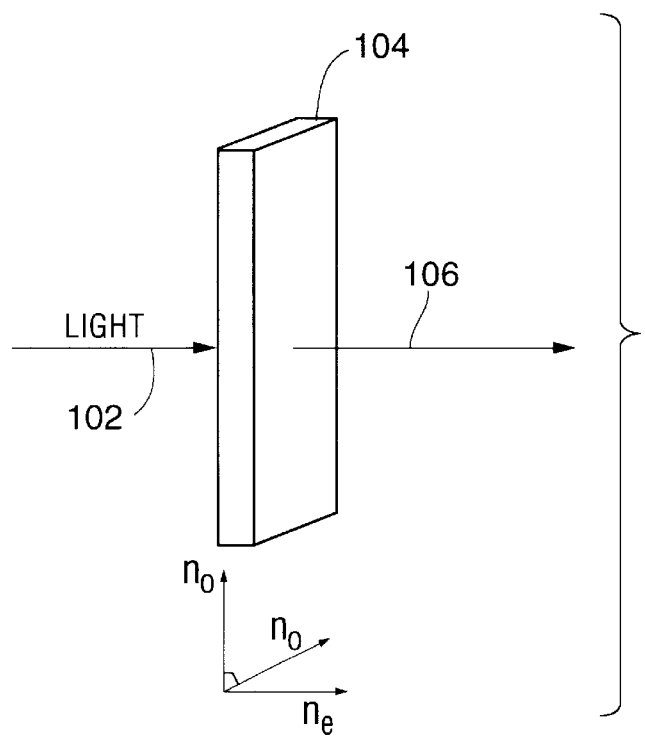
FIGS. 1A and 1B illustrate the operation of a conventional Berek's compensator, where

A particular rotatable-compensator ellipsometer 201 is now described with reference to FIG. 2. The ellipsometer incorporates a novel rotation compensator 208, an embodiment 300 of which is described later with reference to FIG. 3. The ellipsometer 201 simultaneously (or nearly simultaneously) measures the polarization states of a broad range of wavelengths contained in a probe beam reflected from a test sample. The ellipsometer 201, for probing a sample 202, includes a broadband light source 204, a polarizer 206, a rotatable compensator 208, an analyzer 210 and a detector 212.

The light source 204 is, for example, a broadband light source that produces a spectrum of polychromatic light over a predetermined wavelength range of interest. For example, when analyzing semiconductors, one possible predetermined wavelength range of interest would be 200 to 800 nm and may be generated by a high pressure Xe arc lamp to produce a broadband light beam 14 having wavelengths throughout the 200–800 nm wavelength range of interest. The diverging beam 214 from the light source 204 is collimated by a lens 216, such as an achromatic lens or alternately by a focusing mirror.

The beam interacts with polarizer 206 to create a known polarization state. The polarizer 206 may be, for example, a quartz Rochon prism, but in general the polarization does not necessarily have to be linear, or even complete. Polarizer 206 may be made of any of a variety of materials. The azimuth angle of polarizer 206 is oriented so that the plane of the electric vector associated with the linearly polarized beam exiting from the polarizer 206 is at a known angle with respect to the plane of incidence (defined by the propagation direction of the beam 214 and the normal N to the exposed surface of the sample 202). The polarizer 206 can be omitted if a particular light source is used that emits light with the desired known polarization state.

The beam 214 is incident on, and reflects from, sample 202 at an oblique angle. For this discussion, sample 202 is a thin layer 203 formed on a substrate 205. However, in general, the sample 202 can be bare or multiple layers 203 can exist one on top of the other. Based upon well known ellipsometric principles, the reflected beam 215 will generally be elliptically polarized after interacting with the sample 202, as compared to the linear polarization state of the incoming beam 214.

The beam 215 reflected off the sample 202 then passes through a rotatable compensator 208, which introduces a relative phase delay δ (phase retardation) between a pair of mutually orthogonally polarized optical beam components. The amount of phase retardation is a function of the wavelength, the dispersion characteristics of the material used to form the compensator 208, and the thickness of the compensator 208. Compensator 208 is rotated at an angular velocity ω about an axis substantially parallel to the propagation direction of beam 215 (for example, by an electric motor 209).

The compensator 208 is configured such that a desired range of phase retardations of the beam 215 is induced by the range of wavelengths used to probe the sample 202. Beam 215 then interacts with analyzer 210, which serves to mix the polarization states incident on it. Analyzer 210 may be, for example, a linear polarizer oriented at an azimuth angle of 45° relative to the plane of incidence. However, any optical device that serves to appropriately mix the incoming polarization states can be used as an analyzer. The rotatable compensator 208 changes the polarization state of the beam 215 as it rotates in a known way.

Figure 2:
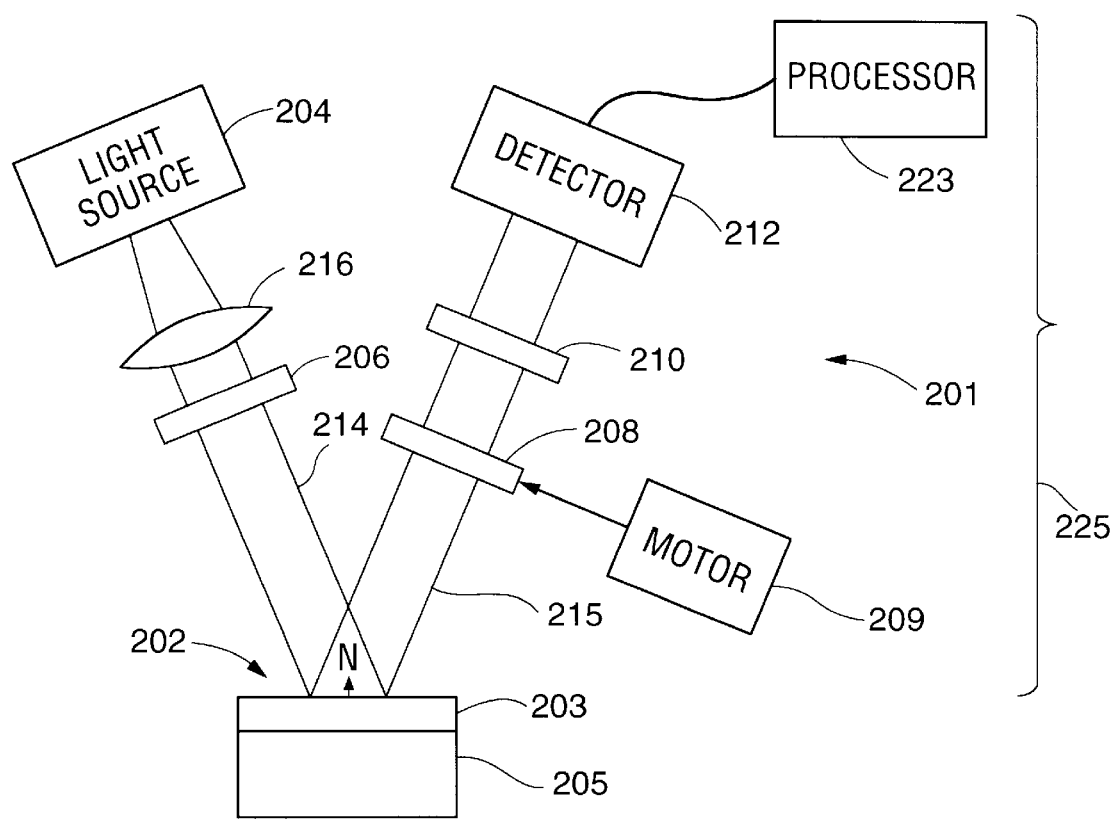
FIG. 2 illustrates a rotatable compensator spectroscopic ellipsometer in which the invention may be embodied.

It should be noted that the compensator 208 can be located either between the sample 202 and the analyzer 210 (as shown in FIG. 2), or between the polarizer 206 and the sample 202. Still further, if the compensator 208 is located between the sample 202, and the analyzer 210, the compensator 208 may be held fixed and the analyzer 210 rotated. On the other hand, if the compensator is located between the polarizer 206 and the sample 202, the compensator 208 may be held fixed and the polarizer 210 rotated. Also, the polarizers could be reflection polarizers in a vacuum for ultraviolet wavelengths.

By measuring the intensity of the light transmitted by analyzer 210, the polarization state of beam 14 reflected from the sample can be determined. In particular, beam 215 enters detector 212, which measures the intensity of the different wavelengths of light throughout the wavelength range of interest that pass through the compensator/analyzer (208/210) combination. Detector 212 may include a dispersive element (not shown), such as a diffraction grating, prism or holographic plate, to angularly disperse the beam 214 as a function of wavelength to individual detector elements contained in a detector array within the detector 212.

Alternately, the detector 212 may be a CCD camera, or a photomultiplier with suitably dispersive or otherwise wavelength selective optics. As yet another alternative, the detector may be include a monochromator, etc., and the different wavelengths may be measured serially (one wavelength at a time) using a single detector element.

A processor 223 processes the intensity information measured by the detector 212 to determine the polarization state of the light after interacting with the analyzer, and the ellipsometric parameters of the sample. This information processing typically not only also includes measuring the beam intensity as a function of wavelength, but also measuring beam intensity as a function of the azimuth (rotational) angle of the compensator about its axis of rotation (which is substantially parallel to the propagation direction of beam 14). This measurement of intensity as a function of compensator rotational angle is effectively a measurement of the intensity of beam 214 as a function of time, since the compensator 208 angular velocity is usually known.

In particular, as is discussed in detail in U.S. Pat. No. 5,877,859 (the disclosure of which is hereby incorporated by reference in its entirety), for example, a rotatable compensator will generate a signal having a dc component, a 2ω (two omega) component and a 4ω (four omega) component with respect to the rotation rate of the compensator. While usable information is generated from both the two omega and four omega signals, it is often felt that the two omega signal is the most significant for analysis. The two omega component is maximized (and, thus, this is the optimum point of operation) when the phase retardation of the compensator is 90 degrees±n*180 degrees, where n is an integer or zero (i.e., |sinδ|=1). Since the phase retardation of the compensator is a function of wavelength, this system lends itself to single wavelength operation only, or to a range where the wavelength changes only by a relatively small amount from the center wavelength of the compensator. As the wavelength deviates from the center wavelength such that the amount of phase retardation induced by the compensator deviates from 90 degrees, the relative intensity of the two omega signal is reduced. Therefore, multiple wavelength operation of rotatable compensator ellipsometers has traditionally been limited to relatively narrow wavelength ranges (less than a factor of two in wavelength) corresponding to substantially 90 degree phase retardations induced by the compensator.

Figure 3:
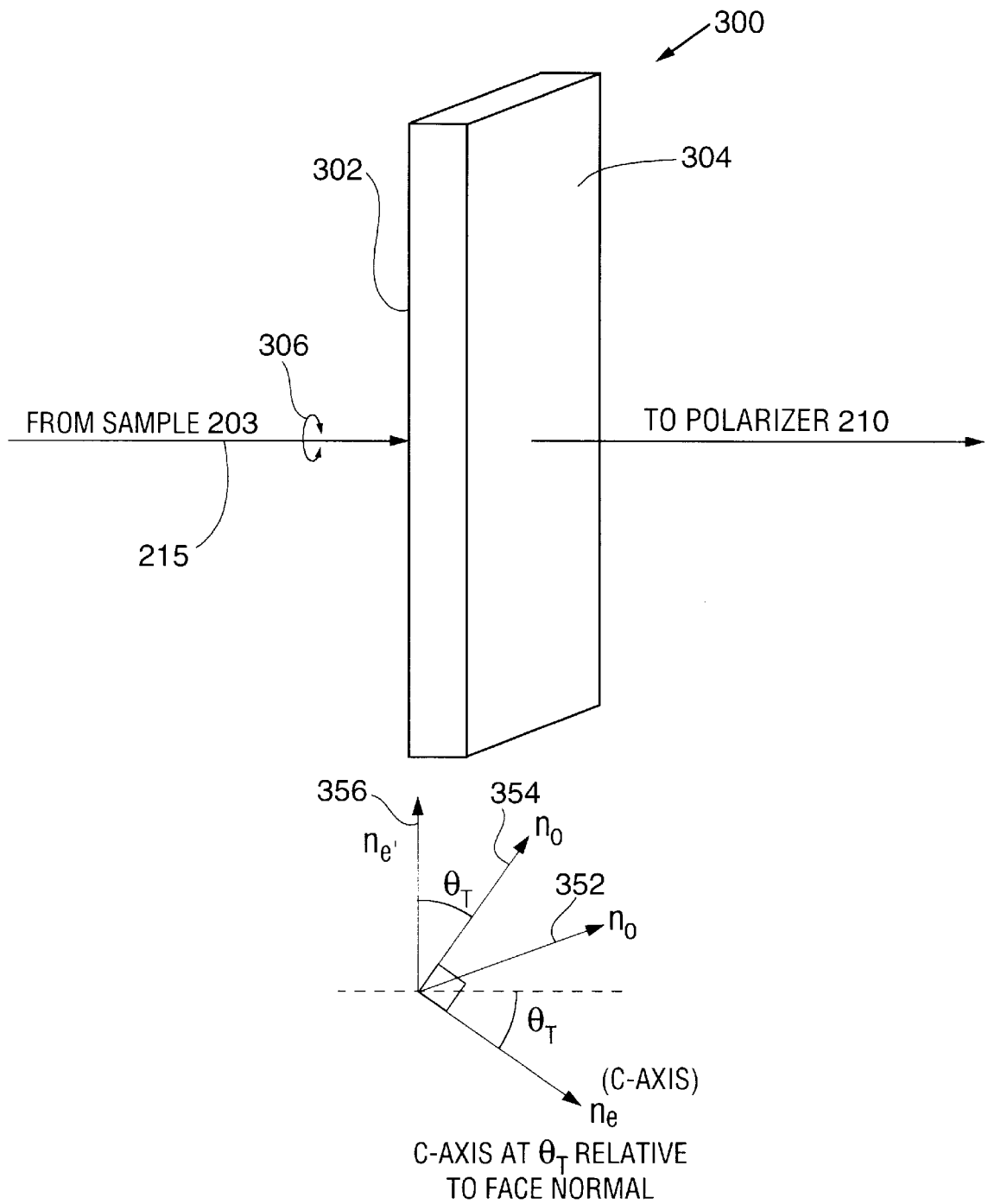
FIG. 3 illustrates a novel compensator particularly useful in rotatable compensator spectroscopic ellipsometers such as the one shown in FIG. 2.

FIG. 3 is a perspective view of one embodiment of an inventive zero-order compensator 300 that may be employed in the FIG. 2 ellipsometer. Like a conventional Berek's compensator, for example, the compensator 300 is formed of a uniaxial crystal (e.g. $MgF_2$). The compensator 300 has a front face 302 onto which the light beam 215 reflected from sample 203 is incident (obscured in the FIG. 3 perspective view) and a rear face 304. Also like a Berek's compensator, the compensator 300 has one ordinary axis (denoted in FIG. 3 by reference numeral 352) parallel to the faces 302 and 304 of the compensator 300. Unlike a Berek's compensator, however, the second ordinary axis (denoted in FIG. 3 by reference numeral 354) of the compensator 300 is not parallel to the faces 302 and 304 of the compensator 300. Rather, the second ordinary axis 354 exists in a plane that is perpendicular to both the faces 302 and 304, and the axis is offset from the front face 302 (and from the rear face 304, for that matter) at an angle denoted in FIG. 3 as $\Theta_T$. Generally (although not always), the angle $\Theta_T$ is less than about ten degrees. As a result, there is an axis 356 perpendicular to the ordinary axis 352 (and parallel to the faces 302 and 304) that is slightly extraordinary, where the amount by which the axis is extraordinary is a function of the angle $\Theta_T$. Thus, somewhat like a Berek's compensator, light incident to the front face 302 will see this slightly extraordinary axis. As the light passes through the compensator 300, it will be slightly phase-retarded.

Thus, with this approach, it is possible to achieve zero-order retardation even with a relatively thick plate. For example, in one demonstration, the specifications of the compensator are as follows:

thickness: (500±3) $\mu$m; and c-axis at (9.50±0.10)° relative to face normal.

The calculated displacement of the slightly extraordinary ray at 632.8 nm is approximately 1.4 $\mu$m. By contrast, the calculated displacement of both rays of a Berek's compensator having the same relative retardance (using mean refractive index squared $n^2=1.91$) is approximately:

$$\Delta x_B \cong \frac{9.5°}{57.3°} * \left(1 - \frac{1}{\sqrt{1.91}}\right) * 500 \ \mu m \cong 22.9 \ \mu m$$

Thus, in accordance with embodiments of the present invention, the displacement in the compensator 300 is reduced to insignificant values. In the preferred embodiment, the compensator has an extraordinary axis offset from the normal to the planar front surface at an angle between one and 15 degrees, with the offset angle and the thickness of the compensator being selected to produce a predetermined zero order retardation for a particular wavelength of the beam as the beam passes completely through the compensator.

Figure 1B:
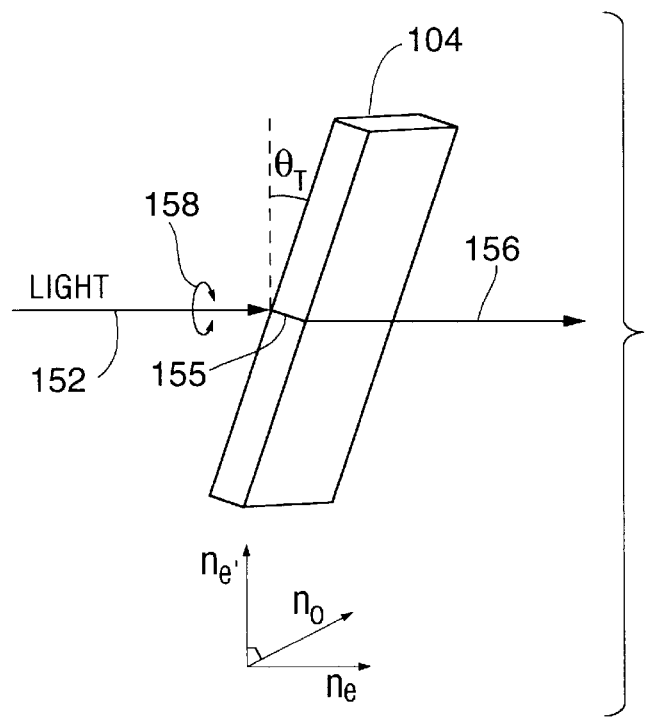

It can be seen that the compensator 300 need not be tilted to achieve a small retardation, such as would a Berek's compensator in use. Because the light beam 215 is normally incident to the compensator 300, the Snell's law displacement phenomena that would be experienced by the FIG. 1B tilted Berek's compensator configuration is eliminated for the ordinary component and minimized for the slightly extraordinary component. Some displacement of the extraordinary component-occurs because energy propagates along a direction perpendicular to the electric and magnetic fields of a beam, and the electric field of the slightly extraordinary beam is slightly tipped relative to the faces of the plate.

The displacement of the extraordinary beam could be reduced even further by slightly tipping the compensator 300. One could thus reduce the displacement of the slightly extraordinary beam by half (although that of the ordinary beam would then be increased—in this case, to have the same value). In use in a rotatable-compensator ellipsometer, the compensator 300 would be rotated as indicated by the arrow 306.

It is to be understood that the present invention is not limited to the particular embodiments described above and illustrated herein. Rather, the invention encompasses any and all variations falling within the scope of the appended claims. For example, as an alternative to rotating the compensator 300, as discussed above, the analyzer 210 may instead be rotated in the axis of the light beam 215 or the polarizer 206 may instead be rotated in the axis of the light beam 214.

Furthermore, the invention is not limited to an ellipsometer with the inventive zero-order compensator. That is, the invention may also encompass a polarimeter alone, such as the polarimeter portion of an ellipsometer. For example, referring to FIG. 2, the polarimeter portion of the ellipsometer is denoted by reference numeral 225, and includes the rotatable compensator 208 (including the motor 209), the analyzer 210, the detector 212 and the processor 223. A polarimeter can be used to analyze the polarization state of any light beam, not just one reflected off a sample such as the sample 202 of FIG. 2.

What is claimed is:

1. An ellipsometer for evaluating a sample, comprising:
    a light generator that generates a beam of light having a known polarization for interacting with the sample;
    a compensator formed of an optically uniaxial crystal having a planar front face and a planar rear face that is substantially parallel to the front face, the compensator having an extraordinary axis offset from a normal to the planar front surface at an angle of at least one degree, with the offset angle and the thickness of the compensator being selected to produce a predetermined zero order retardation for a particular wavelength of the beam as the beam passes completely through the compensator;
    means for rotating the compensator about an axis that is perpendicular to both the front face and to the rear face;
    an analyzer that interacts with the light beam after the light beam interacts with the sample and with the compensator; and
    a detector that measures the intensity of the light after the interaction with the analyzer as a function of an angle of the rotation of the compensator about the axis, wherein the measurements correspond to the polarization state of the light impinging on the analyzer.

2. The ellipsometer of claim 1, wherein the compensator is positioned in the path of the light beam such that the light beam is normally incident to the front face of the compensator.

3. The ellipsometer of claim 1, wherein the compensator is positioned in the path of the light beam such that the light beam is not normally incident to the front face of the compensator.

4. The ellipsometer of claim 3, wherein the compensator is positioned in the path of the light beam such that the light beam is not normally incident to the front face of the compensator, the light beam being incident to the front face of the compensator at an angle such that an extraordinary component of the light beam is displaced by the compensator an amount less than the extraordinary component would be displaced by the compensator if the light beam was normally incident to the front face of the compensator.

5. The ellipsometer of claim 1, wherein the compensator is located between the sample and the analyzer.

6. The ellipsometer of claim 1, wherein the compensator is located between the light generator and the sample.

7. The ellipsometer of claim l, wherein the compensator is a zero order compensator over a range of wavelengths of interest in the beam of light.

8. The ellipsometer of claim 1 wherein the extraordinary axis of the crystal is offset from the normal to the planar front surface at an angle between one and 15 degrees.

9. The ellipsometer of claim 1, wherein the compensator is constituted of a material that is not optically active.

10. The ellipsometer of claim 9, wherein the compensator is constituted of magnesium fluoride.

11. An ellipsometer for evaluating a sample comprising;
    a light source for generating a probe beam of a known polarization state directed to interact with the sample;
    a detector stage for analyzing the change in the polarization state of the beam caused by the interaction with the sample to evaluate the sample; and a rotatable compensator formed from an optically uniaxial crystal for retarding the polarization state of the beam prior to interaction with the detector stage, said compensator having opposed, parallel planar front and rear faces, said compensator having an extraordinary axis offset from a normal to the planar front surface at an angle between one and 15 degrees, with the offset angle and the thickness of the compensator being selected to produce a predetermined zero order retardation for a particular wavelength of the beam as the beam passes completely through the compensator.

12. The ellipsometer of claim 11, wherein the compensator is positioned in the path of the light beam such that the propagation axis of the light beam is normal to the front face of the compensator.

13. The ellipsometer of claim 11, wherein the compensator is positioned in the path of the light beam such that the propagation axis of the light beam is not normal to the front face of the compensator.

14. The ellipsometer of claim 13, wherein the compensator is positioned in the path of the light beam such that the propagation axis of the light beam is not normal to the front face of the compensator, the light beam being incident to the front face of the compensator at an angle such that an extraordinary component of the light beam is displaced by the compensator an amount less than the extraordinary component would be displaced by the compensator if the light beam was normally incident to the front face of the compensator.

15. The ellipsometer of claim 11, wherein the compensator is constituted of a material that is not optically active.

16. The ellipsometer of claim 15, wherein the compensator is constituted of magnesium fluoride.

17. The ellipsometer of claim 11, wherein the compensator is between the sample and the detector stage.

18. The ellipsometer of claim 11, wherein the compensator is between the light source and the sample.

19. The ellipsometer of claim 11, wherein the compensator is a zero order compensator over a range of wavelengths of interest in the beam of light.

20. A polarimeter for evaluating the polarization state of a light beam, comprising:
a compensator formed of an optically uniaxial crystal having a planar front face and a planar rear face that is substantially parallel to the front face, the compensator having an extraordinary axis offset from a normal to the planar front surface at an angle of at least one degree, with the offset angle and the thickness of the compensator being selected to produce a predetermined zero order retardation for a particular wavelength of the beam as the beam passes completely through the compensator;
means for rotating the compensator about an axis that is perpendicular to both the front face and to the rear face;
an analyzer that interacts with the light beam after the light beam interacts with the compensator; and
a detector that measures the intensity of the light after the interaction with the analyzer as a function of an angle of the rotation of the compensator about the axis, wherein the measurements correspond to the polarization state of the light impinging on the analyzer.

21. The polarimeter of claim 20, wherein the compensator is positioned in the path of the light beam such that the light beam is normally incident to the front face of the compensator.

22. The polarimeter of claim 20, wherein the compensator is positioned in the path of the light beam such that the light beam is not normally incident to the front face of the compensator.

23. The polarimeter of claim 22, wherein the compensator is positioned in the path of the light beam such that the light beam is not normally incident to the front face of the compensator, the light beam being incident to the front face of the compensator at an angle such that an extraordinary component of the light beam is displaced by the compensator an amount less than the extraordinary component would be displaced by the compensator if the light beam was normally incident to the front face of the compensator.

24. The polarimeter of claim 20, wherein the compensator is a zero order compensator over a range of wavelengths of interest in the beam of light.

25. The ellipsometer of claim 20 wherein the extraordinary axis of the crystal is offset from the normal to the planar front surface at an angle between one and 15 degrees.

26. The polarimeter of claim 20, wherein the compensator is constituted of a material that is not optically active.

27. The polarimeter of claim 26, wherein the compensator is constituted of magnesium fluoride.

28. A polarimeter for evaluating a sample comprising;
a rotatable compensator formed from an optically uniaxial crystal for retarding the polarization state of the beam, said compensator having opposed, parallel planar front and rear faces, said compensator having an extraordinary axis offset from a normal to the planar front surface at an angle between one and 15 degrees, with the offset angle and the thickness of the compensator being selected to produce a predetermined zero order retardation for a particular wavelength of the beam as the beam passes completely through the compensator; and
a detector stage that detects changes in intensity of the light beam after passing through the compensator, wherein the detected changes correspond to the polarization.

29. The polarimeter of claim 28, wherein the compensator is positioned in the path of the light beam such that the propagation axis of the light beam is normal to the front face of the compensator.

30. The polarimeter of claim 28, wherein the compensator is positioned in the path of the light beam such that the propagation axis of the light beam is not normal to the front face of the compensator.

31. The polarimeter of claim 30, wherein the compensator is positioned in the path of the light beam such that the propagation axis of the light beam is not normal to the front face of the compensator, the light beam being incident to the front face of the compensator at an angle such that an extraordinary component of the light beam is displaced by the compensator an amount less than the extraordinary component would be displaced by the compensator if the light beam was normally incident to the front face of the compensator.

32. The polarimeter of claim 28, wherein the compensator is constituted of a material that is not optically active.

33. The polarimeter of claim 23, wherein the compensator is constituted of magnesium fluoride.

34. The polarimeter of claim 28, wherein the compensator is a zero order compensator over a range of wavelengths of interest in the beam of light.

* * * * *